United States Patent
Weber

(10) Patent No.: US 9,364,141 B2
(45) Date of Patent: Jun. 14, 2016

(54) SHARP FIXATION TARGET

(71) Applicant: Novartis AG, Basel (CH)

(72) Inventor: Marec Weber, Eckental (DE)

(73) Assignee: Novartis AG (CH)

( * ) Notice: Subject to any disclaimer, the term of this patent is extended or adjusted under 35 U.S.C. 154(b) by 0 days.

(21) Appl. No.: 14/548,060

(22) Filed: Nov. 19, 2014

(65) Prior Publication Data

US 2015/0265145 A1 Sep. 24, 2015

(30) Foreign Application Priority Data

Mar. 24, 2014 (DE) .......................... 10 2014 004 248

(51) Int. Cl.
*A61B 3/10* (2006.01)
*A61B 3/02* (2006.01)
*A61B 3/00* (2006.01)
*A61B 3/09* (2006.01)

(52) U.S. Cl.
CPC ................. *A61B 3/0091* (2013.01); *A61B 3/09* (2013.01); *A61B 3/1015* (2013.01)

(58) Field of Classification Search
USPC .................................................. 351/200–246
See application file for complete search history.

(56) References Cited

U.S. PATENT DOCUMENTS

| | | | |
|---|---|---|---|
| 2007/0195264 A1* | 8/2007 | Lai ...................... | A61B 3/0285 351/159.78 |
| 2008/0284979 A1 | 11/2008 | Yee et al. | |
| 2009/0207377 A1* | 8/2009 | Copland ................ | A61B 3/103 351/221 |
| 2012/0002163 A1 | 1/2012 | Neal | |
| 2015/0131054 A1* | 5/2015 | Wuellner ............. | A61B 3/0025 351/211 |

FOREIGN PATENT DOCUMENTS

| | | |
|---|---|---|
| DE | 2412059 C2 | 7/1988 |
| DE | 102005035870 A1 | 2/2007 |
| JP | 2005021181 A | 1/2005 |

* cited by examiner

*Primary Examiner* — Mohammed Hasan

(57) ABSTRACT

A device for stabilizing the constant accommodation of an eye comprises a target object, an optical unit, and an additional optical unit. The target object is set up to be fixatated by a patient along an optical axis. The optical unit is set up along the optical axis to compensate for a spherical ametropia of the eye. The additional optical unit is set up along the optical axis to compensate for an astigmatic ametropia of the eye. The additional optical unit comprises at least two cylindrical lenses and at least four deflection prisms. At least one cylindrical lens is rotatably arranged about the optical axis. At least one deflection prism can be adjusted to change the optical path length of the light path from the target object to the eye.

14 Claims, 4 Drawing Sheets

Z=cylinder compensation
L=lens or lens system
A=eye

Z=cylinder compensation
L=lens or lens system
A=eye

| RMS values | RMS g | | | | | |
|---|---|---|---|---|---|---|
| | RMS 1 | RMS 2 | RMS h | | | |
| | | | RMS 3 | RMS 4 | RMS 5 | RMS 6 |
| Aberrat. type | Low order aberrat. | | Higher order aberrat. (HOA) | | | |
| Zernike order | 1 | 2 | 3 | 4 | 5 | 6 |
| 3D image |  |  |  |  |  |  |

SHARP FIXATION TARGET

CROSS REFERENCE TO RELATED APPLICATIONS

This application claims priority to German Patent Application Serial No. 102014004248.0, filed Mar. 24, 2014, the entire contents of which are incorporated herein by reference.

TECHNICAL FIELD

The invention relates to a device offering a patient a sharp fixation target, for fixation on a diagnostic or therapeutic apparatus, independently of low-aberration sight defects of the patient. The term "sharp fixation target" here does not refer to the target itself, but to the sharpness of the representation in the perception of the patient.

BACKGROUND

In numerous ophthalmological measurements and/or surgical interventions, the constant accommodation of a patient's eye is stabilized by offering the patient a target object (so-called target), typically in the form of a light source. The patient fixates (sights, looks at) this light source without interruption. In the process, the patient will unintentionally attempt to see the target object (target) sharply. However, if the fixating eye has aberrations, the focusing can only occur more or less incompletely.

The known devices for the fixation of an eye according to the prior art take into account an ametropia of the eye only in terms of focusing relative to defocus, that is blurriness, which results from obtaining a sharp representation of a point to be pictured in front of or behind the retina. Such defocus is referred to as a low order aberration. In ophthalmology, the imaging properties of the eyes are usually represented with so-called Zernike polynomials. The defocus relates to the Zernike polynomial Z4 (see FIG. 4). In the prior art, an attempt is made to reduce the defocus during fixation, for example, by shifting the lenses or lens systems and/or by shifting the target object for the purpose of increasing or shortening the object distance.

SUMMARY OF EXAMPLE EMBODIMENTS

The present invention is based on the finding that the currently offered solution in the prior art, in particular the correction of the blurriness of the fixation target based on defocus, does not make it possible for the patient to see the fixation target consistently sharply, in the case of the presence of further low order aberrations, so that, if queried, the patient generally indicates satisfaction with the least blurry result for psychological reasons.

The fixation solution offered by the prior art in addition leads to inaccuracies with regard to both the measurement of the eye and an ophthalmological intervention. In the described prior art, the patient, in case further aberrations are present, for example, an astigmatism, can discern the target object (target) sharply always in only one main plane direction. This leads to a permanent change in the accommodation between the two main sections, or main planes, so that the patient cannot see the fixation target accurately or he/she can see it only with incomplete sharpness. As a result of the permanent change in accommodation, the measurement results are biased.

The invention is based on the problem of offering a method and a device for stabilizing the constant accommodation of the patient's eye in the case of aberrations other than the defocus aberrations, in order to present the sharpest possible fixation target to the patient, and as a result allow not only a stable accommodation position but also improved measurement results with regard to the optical and anatomic properties of the eyes.

In this context, the invention provides a method and a device for stabilizing the constant accommodations of a patient's eye, comprising:
- a target object which is arranged to be fixated by the patient along an optical axis
- an optical unit in the light path, which is arranged and set up on the optical axis, for the purpose of compensating a lower order ametropia, for example, a spherical ametropia of the eye, partially or completely depending on the adjustment of the optical unit 14, and
- an additional optical unit in the light path, by means of which a higher order ametropia, for example, an astigmatic ametropia of the eye, can be compensated partially or completely depending on the adjustment of the optical unit 14.

The method according to the invention entails in particular the following steps:
- a target object is arranged so that it can be fixated by a patient along an optical axis,
- an optical unit is arranged on the optical axis, in order to compensate thereby a lower order ametropia of the eye, for example, a spherical ametropia, partially or completely depending on the adjustment of the optical unit 14, and
- an additional optical unit is arranged in the light path, in order to compensate thereby an ametropia of higher order, for example, an astigmatic ametropia of the eye, partially or completely depending on the adjustment of the optical unit 14.

The invention makes it possible, in particular, to provide the mentioned device as an automated device, wherein the mentioned optical units do not necessarily have to be actuated by hand (wherein simple designs can definitely allow a manual intervention).

In particular, the device and the method according to the invention are suitable for stabilizing the accommodation of the eye in the case of the presence of additional low order aberrations (in addition to defocus).

According to a design of the invention, one of the optical units can comprise at least two optical components, for example, cylindrical lenses with toric effect, which are rotatably mounted according to another design of the invention around the optical axis. However, in an alternative design of the invention, it is also conceivable to focus the fixation target by means of several lenses with toric effect.

If the above-mentioned optical units comprise two or more cylindrical lenses, then they can have both a positive refraction power and also a negative refraction power. In a particular design of the invention, at least one cylindrical lens has a positive refraction power, while at least one additional cylindrical lens, preferably arranged opposite, has a negative refraction power. In a further embodiment of the invention, depending on the application, it is also possible for at least two of the cylindrical lenses to have a positive refraction power or equivalent negative refraction power.

In addition, the invention provides a device for measuring an eye, wherein the above-mentioned device for stabilizing in particular constant accommodation of an eye in an aberrometer, can be coupled into an aberrometer, an autorefractometer, a biometer or other diagnostic or therapeutic apparatus. Aberrometers as such are well known in the ophthalmological technology. For example, Hartmann-Shack and also Tscherning aberrometers are commonly used.

In addition to providing a sharp fixation target, the invention also promotes the accuracy and reliability of a measurement of the eye, using, for example, an aberrometer, as well as the stability of the fixation of an eye during an ophthalmological intervention, compensating not only the defocus, but also astigmatic ametropia.

By taking into consideration the sphero-cylindrical ametropia of the patient's eye during the sighting of the target object provided, it is possible to reduce to a minimum or completely eliminate the accommodation fluctuations and the ametropia of the patients that are the result of 2nd order aberrations by means of the above-described features of the invention.

BRIEF DESCRIPTION OF THE DRAWINGS

Possible embodiments of the invention are further explained below in reference to the figures.

DETAILED DESCRIPTION OF THE DRAWINGS

Figure 1:
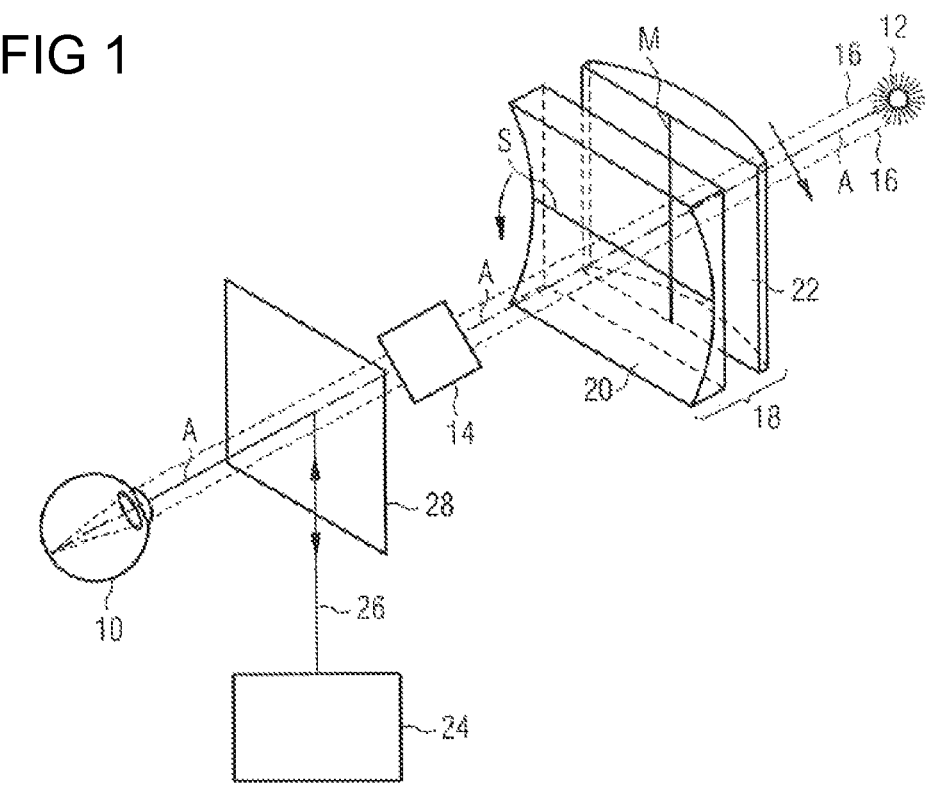
FIG. 1 diagrammatically shows a device for measuring an eye, in particular the imaging properties of the eye.

FIG. 1 shows a diagrammatic representation of the automatic focusing, according to the invention, of a target object 12 for at least one eye 10. Here, the target object 12 can be illuminated or it can itself emit light by means of a light beam 16. The target object 12 is pictured in the eye 10 here in a manner which is known per se by means of an optical unit 14. The optical unit 14 corrects, in a known manner, a possible defocus Z4 of the eye 10. In a preferred embodiment, the optical unit 14 can be a lens system (not further represented), which is shifted automatically for the purpose of minimizing the defocus Z4 along the optical axis A, by means of actuators (not shown), individually for the patient, so that the patient can perceive the target object in accurate form.

In the represented embodiment example of the invention, an additional optical unit 18 consists of at least two cylindrical lenses 20, 22, which, in the represented starting position, are oriented mutually orthogonally, i.e., the sagittal line S of one cylindrical lens 20 is perpendicular to the meridional line M of the other cylindrical lens 22. In the represented 90° position of the cylinder axes of the two cylindrical lenses 20, 22, the total cylinder power is equal to zero if the contribution of the two cylinders is of equal amount. The cylindrical lenses 20, 22 in each case are rotatably mounted individually or also jointly around the optical axis A of the overall system. By an appropriate rotation, the position of the lenses with respect to one another can be changed and thus the total cylinder power can be adjusted as desired, particularly for compensating a plano-cylindrical or sphero-cylindrical ametropia of the patient. In a further preferred design of the invention, the common rotation of the two lenses influences the axis position of the resulting cylinder of the two individual systems.

Furthermore, FIG. 1 shows the above-described device for stabilizing the constant accommodation of the patient's eye in the case of 2nd order aberrations, which is completed by a measurement device 24, a Hartmann-Shack aberrometer in the embodiment example represented here. On the optical axis A of the fixation device formed by the target object 12, the optical unit 14, and the additional optical unit 18, a beam splitter 28, for example, a semi-transparent mirror, is arranged, which reflects the measurement radiation 26 of the measurement device 24 along the axis A into the eye 10, and also the measurement radiation 26 coming from the eye in the opposite direction toward the measurement device 24. Likewise, the beam splitter 28 is transparent to the light beam 16 of the target object 12.

In the represented embodiment example, the additional optical unit 18 comprises two cylindrical lenses 20, 22 in which the amount of the cylinder power is identical. Due to the rotation of the two lenses, in opposite directions or in the same direction as desired, the cylinder axis can be corrected. By an appropriate rotation and thus angular setting of the cylindrical lenses with respect to one another, the total cylinder power can be adjusted. In total, a maximum cylinder compensation of the astigmatic defect of the eye can be achieved thereby.

Figure 2:
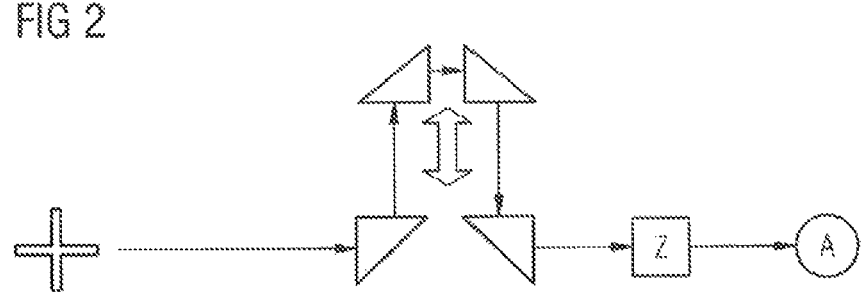
FIG. 2 shows a diagrammatic representation of an automatic focusing of the target.

Based on the explanations of FIG. 1, FIG. 2 shows a diagrammatic representation of a preferred embodiment of an automatic focusing of the target. For this purpose, the additional optical unit 18, in addition, comprises at least four deflection prisms 32-35, wherein these prisms are arranged so that they can be adjusted individually or in pairs together, as represented by the arrow 30. By means of this design, the optical path length is changed due to the mechanical movement path of the upper two prisms 33, 34.

Figure 3:
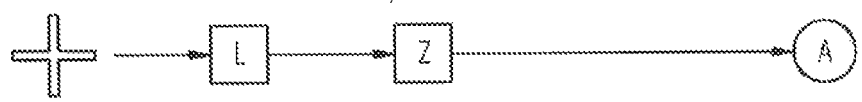
FIG. 3 shows a diagrammatic representation of an additional embodiment of an automatic focusing of the target.

Based on the explanations of FIG. 1, FIG. 3 shows a diagrammatic representation of an additional preferred embodiment of an automatic focusing of the target. Here, in contrast to FIG. 1, the arrangement of the optical unit 14 is replaced with the arrangement of the additional optical unit 18. As a result of the optical units being arranged next to one another, they can be mounted in a manner so that they can be moved with respect to one another by means of actuators, in order to adjust the image position, in particular the far point of the individual eye, fully automatically by means of actuators.

In this manner, it is possible to dispense with feedback from the patient regarding the perceived focusing of the target object, because a sharp fixation target adjusted especially for the existing ametropia is automatically presented to the patient. As a result, the fixation of the eye achieves the maximum possible constant stability.

Figure 4:
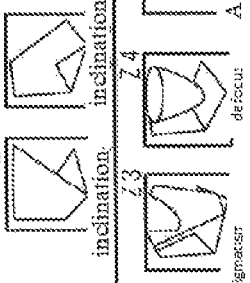
FIG. 4 diagrammatically shows the pictorial representation of the Zernike polynomial, for the purpose of describing the imaging properties of the eye.
Figure 4:
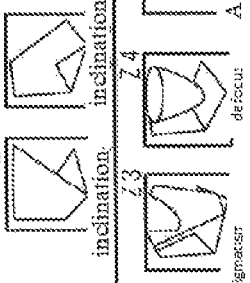
Figure 4:
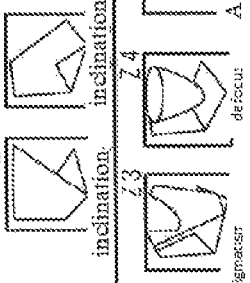
Figure 4:
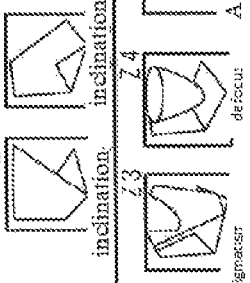
Figure 4:
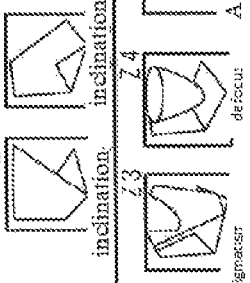
Figure 4:
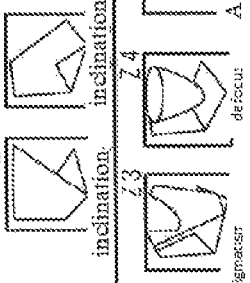

FIG. 4 diagrammatically shows the pictorial representation of the Zernike polynomial, for the purpose of describing the imaging properties of the eye. As already explained above, it is already known in the prior art to adjust the eye of the patient by orienting it towards a target object in order to conduct diagnostic measurements. For this purpose the tilt (inclination) Z1 and Z2 is achieved by lining up the patient in front of the target object, and the defocus Z4 is also achieved by a shifting the lens systems. According to the invention, the astigmatism Z3 and Z5 is taken into account in a new way, so that a target object having the above-described features of the invention can be provided, so that the individual accommodation variations of the respective patient are eliminated and an ametropia of the patient caused by $2^{nd}$ order aberrations is completely corrected.

Figure 5:
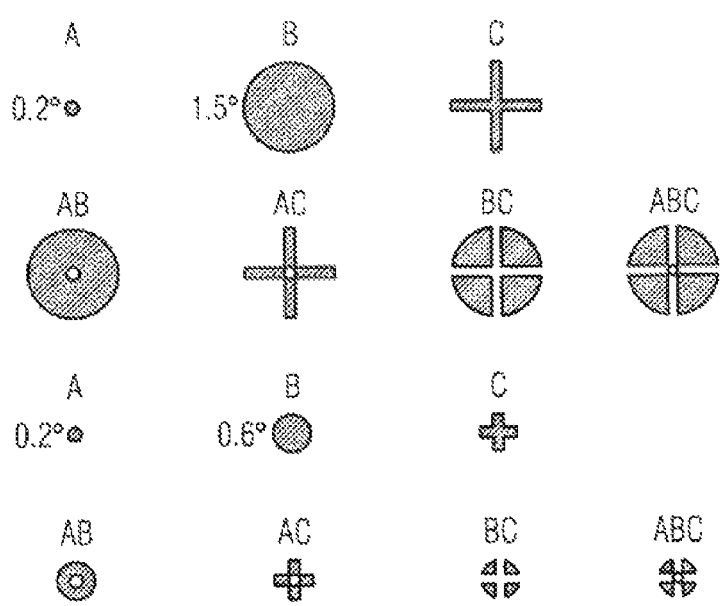
FIG. 5 diagrammatically shows possible embodiments of the target object.

FIG. 5 diagrammatically shows possible designs of the target object 12, which are used as a variant of the possibility represented in FIG. 3. Here, the target object 12 can be illuminated, or it can itself emit light by means of a light beam 16, so that special patterns can be perceived by the patient, which can also vary during the fixation, in order to maintain the concentration of the patient. In particular, a pattern can be configured to be perpendicular (or in any other angular arrangement) relative to the optical axis A with radially outward extending light segments (as indicated in FIG. 3). Alternative geometric embodiment variants of the target objects can be seen in FIG. 5. Additional geometric shapes are also available to the person skilled in the art, such as, for example, stellate, round, elliptic shapes or polygonal bodies of any shape.

The described invention can be used in all ophthalmological apparatuses in which the best possible quality of correction of the eye to be measured is to be achieved. Undesired secondary effects, such as accommodation or accommodation-induced spherical aberrations are largely prevented.

The invention claimed is:

1. Device for stabilizing the constant accommodation of an eye of a patient, comprising:
    a target object that is set up to be fixated by the patient along an optical axis;
    an optical unit in the light path from the target object to the eye, the optical unit set up along the optical axis in order to compensate for a spherical ametropia of the eye; and
    an additional optical unit in the light path, the additional optical unit set up along the optical axis in order to compensate for an astigmatic ametropia of the eye, the additional optical unit comprising:
        at least two cylindrical lenses, wherein at least one cylindrical lens is rotatably arranged about the optical axis; and
        at least four deflection prisms, wherein at least one deflection prism can be adjusted to change the optical path length of the light path from the target object to the eye.

2. Device according to claim 1, wherein a first cylindrical lens has a positive refraction power and a second cylindrical lens has a negative refraction power.

3. Device according to claim 1 wherein two cylindrical lenses have positive refraction power.

4. Device according to claim 1, wherein two cylindrical lenses have negative refraction power.

5. Device according to claim 1, further comprising an aberrometer that can measure the eye.

6. Device according to claim 5, wherein the aberrometer is a Hartmann-Shack aberrometer.

7. Device according to claim 5, wherein the aberrometer is a Tscherning aberrometer.

8. Method for stabilizing the constant accommodation of an eye of a patient, with the following steps:
    arranging a target object so that it can be fixated by the patient along an optical axis;
    compensating for a spherical ametropia of the eye with an optical unit along the optical axis; and
    compensating for an astigmatic ametropia of the eye, with an optical unit along the optical axis by:
        rotating at least one cylindrical lens of at least two cylindrical lenses about the optical axis; and
        adjusting at least one deflection prism of at least four deflection prisms to change the optical path length of the light path from the target object to the eye.

9. Method according to claim 8, wherein a first cylindrical lens has a positive refraction power and a second cylindrical lens has a negative refraction power.

10. Method according to claim 8, wherein two cylindrical lenses have positive refraction power.

11. Method according to claim 8, wherein two cylindrical lenses have negative refraction power.

12. Method according to claim 8, further comprising measuring the eye with an aberrometer.

13. Method according to claim 12, wherein the aberrometer is a Hartmann-Shack aberrometer.

14. Method according to claim 12, wherein the aberrometer is a Tscherning aberrometer.

* * * * *